United States Patent [19]

Yoshikawa et al.

[11] Patent Number: 4,885,286

[45] Date of Patent: Dec. 5, 1989

[54] PHOSPHONAMIDOTHIONATE DERIVATIVES AND THEIR USE AS PESTICIDES

[75] Inventors: Hiromichi Yoshikawa, Fukuoka; Teruyuki Misumi, Yokohama, both of Japan

[73] Assignee: Asahi Kasei Kogyo Kabushiki Kaisha, Osaka, Japan

[21] Appl. No.: 157,934

[22] Filed: Feb. 19, 1988

[51] Int. Cl.$^4$ .......................... A01N 57/26; C07F 9/32; C07F 9/65

[52] U.S. Cl. ...................................... 514/120; 514/92; 548/111; 558/138; 558/181

[58] Field of Search ................ 558/181, 138; 514/120, 514/92; 548/111

[56] References Cited

U.S. PATENT DOCUMENTS 4,168,305  9/1979  Maurer et al. ...................... 558/181
4,662,930  5/1987  Gray et al. .............................. 71/87
4,683,224  7/1987  Fahmy ................................ 514/120

FOREIGN PATENT DOCUMENTS 164308  4/1985  European Pat. Off. .
93792  4/1988  Japan ................................ 558/181

OTHER PUBLICATIONS

Derkash et al., "Chem. Abst.", vol. 68, (1968), 59664b.
Kondratyuk et al., "Chem. Abst.", vol. 73, (1973) 12762v.

Primary Examiner—Anton H. Sutto
Attorney, Agent, or Firm—Birch, Stewart, Kolasch & Birch

[57] ABSTRACT

A novel phosphonamidothionate derivative represented by the formula

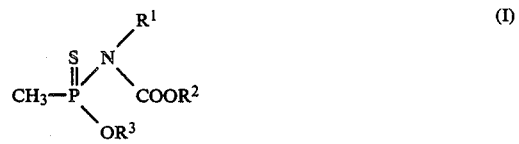

wherein $R^1$, $R^2$ and $R^3$ are as defined in the disclosure. The present novel compound has excellent properties with respect to not only pesticidal activity but also maintenance of the pesticidal activity over a prolonged period of time after application. The present novel compound can be prepared by a new unique process in which the direct phosphorylation of a carbamate compound is involved.

12 Claims, No Drawings

PHOSPHONAMIDOTHIONATE DERIVATIVES AND THEIR USE AS PESTICIDES

BACKGROUND OF THE INVENTION

1. Field of the Invention

The present invention relates to a novel phosphonamidothionate derivative and a process for the preparation thereof. The present invention also relates to a pesticidal composition containing the novel compound and a method for combatting insect pests. More particularly, the present invention is concerned with a novel phosphonamidothionate derivative represented by the formula

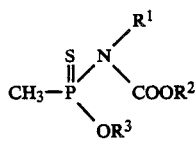

wherein $R^1$ and $R^2$ each independently represent a straight-chain alkyl group having 1 to 4 carbon atoms or a branched alkyl group having 3 or 4 carbon atoms and $R^3$ represents a phenyl group unsubstituted or substituted with a chlorine atom, a methyl group, a nitro group, a methylthio group or a nitrile group, an alkyl group having 1 to 4 carbon atoms or a 5-methyl-2-isoxazolyl group. The novel compound is characterized by a high pesticidal activity which lasts for a long period of time after application. The present invention is also concerned with a unique process for preparing the phosphonamidothionate derivative, in which the direct phosphorylation of a carbamate compound is involed, a pesticidal composition comprising as an active ingredient the above-mentioned novel compound and a method for combatting sanitary insect pests, or agricultural and horticultural insect pests by using the compound.

2. Discussion of Related Art

Various organophosphorus pesticides, carbamate pesticides and pyrethroid pesticides are used for combatting agricultural insect pests. However, none of the conventional pesticides have a long lasting effect after application. In general, if a pesticide is applied to farm land, the crops on the farm land are protected only for the period in which the pesticide remains active. This is because there are some insect pests on farm land which are not killed by the application of the pesticide, and these insect pests harm the crops when the pesticidal activity of the pesticide is lost. In addition, when the activity of the pesticide is lost, insect pests fly from the neighboring farm lands into the farm land and harm the crops thereon. Accordingly, for protecting crops by using a conventional pesticide in regions where insect damage frequently occurs, it is required to repeat the application of the pesticide at short intervals. This necessitates a considerable amount of labor, leading to great disadvantages.

U.S. Pat. No. 4,683,224 discloses the pesticidal activity of an N-formyl phosphonamidothionate which has such a chemical structure as is obtained by substituting, in the chemical structure of formula (I), a group of the formula —$SR^3$ for the group of the formula —$OR^3$, formamide for the carbamate moiety and a P=O bond for the P=S bond. European Patent Application Laid-Open Specification No. 0 164 308 discloses the pesticidal activity of an N-formyldithiophosphonic acid amide which has such a chemical structure as is obtained by substituting, in the chemical structure of formula (I), a group of the formula —$SR^4$, wherein $R^4$ represents an alkyl group or an alkenyl group, for the group of the formula—$OR^3$ and formamide for the carbamate moiety. U.S. Pat. No. 4,168,305 discloses the pesticidal activity of an S-alkyl-N-carbonyl-alkanedithiophosphonic acid ester amide which has such a chemical structure as is obtained by substituting, in the chemical structure of formula (I), a hydrogen atom for the alkyl group represented by $R^1$ and a group of the formula —$SR^5$, wherein $R^5$ represents an alkyl group, for the group of the formula —$OR^3$. However, these conventional compounds are not satisfactory with respect to pesticidal activity.

Further, there is known a compound which has such a chemical structure as is obtained by substituing, in the chemical structure of formula (I), a hydrogen atom for the alkyl group represented by $R^1$ (see, for example, Zh. Obshch. Khim. Vol. 37, 2069 (1967) and Fiziol. Aktiv. Veshchestva 1969, No. 2, 37). However, this compound is not satisfactory with respect to pesticidal activity, as set forth in the Examples hereinbelow.

SUMMARY OF THE INVENTION

With a view toward developing a novel compound which not only exhibits a high pesticidal activity but also maintains the high pesticidal activity for a prolonged period of time after application, the present inventors have made extensive and intensive studies. As a result, the present inventors have unexpectedly found that novel phosphonamidothionate derivatives can be prepared by a new unique process and that they have excellent properties with respect to pesticidal activity and maintenance of the pesticidal activity. Based on these novel findings, the present invention has been completed.

Accordingly, it is an object of the present invention to provide a novel phosphonamidothionate derivative which not only exhibits a high pesticidal activity but also maintains the high pesticidal activity for a prolonged period of time after application.

It is another object of the present invention to provide a unique process for preparing the novel compound.

It is still another object of the present invention to provide a pesticidal composition comprising the compound.

It is a further object of the present invention to provide a method for combatting insect pests by using the compound.

DETAILED DESCRIPTION

In one aspect of the present invention, there is provided a phosphonamidothionate derivative represented by the formula

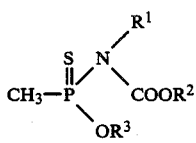

wherein $R^1$ and $R^2$ each independently represent a straight-chain alkyl group having 1 to 4 carbon atoms or a branched alkyl group having 3 or 4 carbon atoms, and $R^3$ represents a phenyl group unsubstituted or substituted with a chlorine atom, a methyl group, a nitro group, a methylthio group or a nitrile group, an alkyl group having 1 to 4 carbon atoms or a 5-methyl-2-isoxazolyl group.

From the viewpoint of the desired effect of combatting sanitary and, agricultural and horticultural insect pests such as *Musca spp., Laodelphax striatellus, Nephotettix cincticeps, Myzus persicae, Prodenia litura* and *Plutella maculipennis.* it is preferred in the compound of the present invention that $R^1$ is a straight-chain alkyl group having 2 or 3 carbon atoms or an isopropyl group, $R^2$ is a straight-chain alkyl group having 2 or 3 carbon atoms or a branched alkyl group having 3 or 4 carbon atoms and $R^3$ is a 4-nitrophenyl group, a 3-methyl-4-nitrophenyl group, a 4-cyanophenyl group, an ethyl groups or a 5-methyl-2-isoxazolyl group. Of the compounds having the above-mentioned substituents, a compound in which $R^1$ and $R^2$ each represent a isopropyl group and $R^3$ is a 4-nitrophenyl group is most preferred. This compound is referred to in the later given Examples as compound No. 47.

In another aspect of the present invention, there is provided a process for preparing a phosphonamidothionate derivative represented by the formula

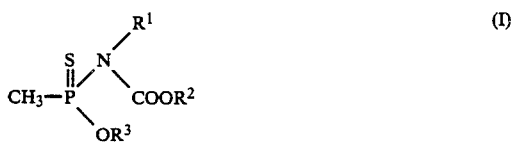

(I)

wherein $R^1$ and $R^2$ each independently represent a straight-chain alkyl group having 1 to 4 carbon atoms or a branched alkyl group having 3 to 4 carbon atoms and $R^3$ represents a phenyl group unsubstituted or substituted with a chlorine atom, a methyl group, a nitro group, a methylthio group or a nitrile group, an alkyl group having 1 to 4 carbon atoms or a 5-methyl-2-isoxazolyl group, which comprises the steps of (1) reacting a carbamic acid ester derivative represented by the formula

(II)

wherein $R^1$ and $R^2$ each independently represent a straight-chain alkyl group having 1 to 4 carbon atoms or a branched alkyl group having 3 or 4 carbon atoms, with methylphosphonothioic dichloride in dioxane in the presence of an amine, to thereby obtain a methylphosphonothioyl chloride derivative represented by the formula

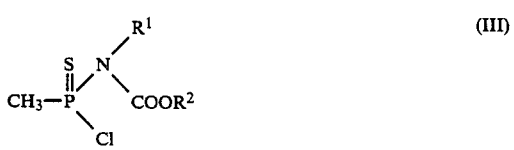

(III)

wherein $R^1$ and $R^2$ are as defined above, and (2) subsequently reacting the methylphosphonothioyl chloride derivative of formula (III) with a compound represented by the formula

wherein $R^3$ represents a phenyl group unsubstituted or substituted with a chlorine atom, a methyl group, a nitro group, a methylthio group or a nitrile group, an alkyl group having 1 to 4 carbon atoms or a 5-methyl-2-isoxazolyl group, in tetrahydrofuran in the presence of an amine.

The process of the present invention comprises two steps. The reactions respectively involved in the two steps will be referred to as reaction (1) and reaction (2), respectively.

In reaction (1), the carbamic acid ester derivative of formula (II) is reacted with methylphosphonothioic dichloride in dioxane in the presence of an amine under reflux, to thereby obtain a methylphosphonothioyl chloride derivative of formula (III). The amine to be employed in reaction (1) is preferably a trialkylamine, most preferably triethylamine. Reaction (1) proceeds most efficiently when the molar ratio between the carbamic acid ester derivative, methylphosphonothioic dichloride and the amine is 1:1:1. However, reaction (1) proceeds even if any one or two of the reactants are employed in excess. Generally, the molar ratio of one reactant to any of the other two reactants may be in the range of ¼:1 to 4:1. The amount of dioxane used in reaction (1) is preferably 600 to 1200 ml per mole of the phosphonothioic dichloride. Sufficiently dehydrated dioxane is used for reaction (1). Reaction (1) is conducted at a temperature at which dioxane can be refluxed, i.e. at about 101° C. (the boiling point of dioxane) or higher. A methylphosphonothioyl chloride derivative is formed by reaction (1).

In reaction (2), the methylphosphonothioyl chloride derivative obtained in reaction (1) is reacted with a compound of formula (IV) in a solvent in the presence of an amine, to thereby obtain the compound of the present invention. The amine to be employed in reaction (2) is preferably a trialkylamine, most preferably triethylamine. The solvent may be any of those solvents which are generally used in organochemical syntheses. Of those solvents, sufficiently dehydrated tetrahydrofuran is especially preferable. Reaction (2) proceeds most efficiently when the ratio of the methylphosphonothioyl chloride derivative to the compound of formula (IV) is 1:1 and the amine is employed in excess. However, reaction (2) proceeds even if any one or both of the methylphosphonothioyl chloride and the compound of formula (IV) are in excess. Generally, the molar ratio of one reactant to any of the other two reactants may be in the range of ¼:1 to 4:1. In case tetrahydrofuran is used as the solvent, the amount thereof may preferably be 3000 to 5000 ml per mole of the compound of formula (IV). Reaction (2) may preferably be conducted at a temperature in the range of 0° C. to room temperature. Reaction (2) is carried out while stirring the mixture of the reactants and the solvent.

The above-mentioned two reactions respectively in the two steps proceed slowly. With respect to each of reactions (1) and (2), the reaction product consists only of the desired product in most cases. In case impurities are contained in the reaction product, such impurities may be removed by a conventional purifying method, such as column chromatography. With respect to control of the reaction time in each of reactions (1) and (2), it is preferable to check the progress of the reaction by thinlayer chromatography and terminate the reaction at an appropriate stage. In general, the reaction time may be 1 to 4 hours for reaction (1) and 10 to 24 hours for reaction (2).

The most characteristic feature of the process of the present invention resides in that a carbamic acid ester derivative represented by formula (II) is reacted with methylphosphonothioic dichloride in dioxane in the presence of an amine under reflux, to thereby obtain the compound represented by formula (III). Conventionally, as a method for synthesizing a phosphonamidothionate derivative, there is known a method in which a phosphoric acid amide obtained from phosphoryl isocyanate is converted to a compound having such a chemical structure as is obtained by substituting, in the chemical structure of formula (I), a hydrogen atom for the alkyl group represented by $R^1$, and the resultant compound is then reacted with an alkylating agent to effect alkylation at the nitrogen atom of the amide. However, by this method, the compound of the present invention, i.e. the phosphonamidothionate derivative having the chemical structure represented by formula (I) cannot be obtained. Further, it is noted that there have been no reports that direct phosphorylation of a carbamate compound has successfully been conducted. It is quite surprising that a novel phosphonamidothionate derivative of formula (I) has successfully been synthesized by the process of the present invention which is simple as described above.

The phosphonamidothionate derivative of the present invention is well tolerated by plants and can be employed for combatting insect pests which are encountered in agriculture, in forestry, in the protection of stored agricultural products, and in the hygiene field. The phosphonamidothionate derivative of the present invention is active against normally resistant species as well as normally sensitive species, and is active against all or certain stages of growth, depending on the species.

Accordingly, in further aspects of the present invention, there are provided a pesticidal composition comprising as an active ingredient a pesticidally effective amount of a phosphonamidothionate derivative represented by formula (I) and a sanitary or agriculturally and horticulturally acceptable carrier or diluent, and a method for combatting sanitary inspect pests or agricultural and horticultural insect pests, which comprises applying to the insect pests or a habitat thereof a pesticidally effective amount of a phosphonamidothionate derivative represented by formula (I).

The pests which are controllable by the action of the compound of the present invention include:

from the order of the Orthoptera, for example *Periplaneta americana*, *Blattella germanica* and *Locusta migratoria migratorioides*;

from the order of the Isoptera, for example *Reticulitermes spp.*;

from the order of the Mallophaga, for example *Trichodectes spp.* and *Damalinea spp.*;

from the order of the Thysanoptera, for example *Hercinothrips femoralis* and *Thrips tabaci*;

from the order of the Heteroptera, for example *Eurygaster spp.* and *Cimex lectularius*;

from the order of the Homoptera, for example *Bemisia tabaci*, *Aphis gossypii*, *Brevicoryne brassicae*, *Eriosoma lanigerum*, *Hyalopterus arundinis*, *Macrosiphum avenae*, *Myzus spp.*, *Phorodon humuli*, *Rhopalosiphum padi*, *Empoasca spp.*, *Nephotettix cincticeps*, *Lecanium corni*, *Laodelphax striatellus*, *Nilaparvata lugens*, *Aonidiella aurantii*, *Aspidiotus hederae* and *Psylla spp.*;

from the order of the Lepidoptera, for example *Pectinophora gossypiella*, *Plutella maculipennis*, *Malacosoma neustria*, *Euproctis chrysorrhoea*, *Lymantria spp.*, *Phyllocnistis citrella*, *Agrotis spp.*, *Laphygma exigua*, *Mamestra brassicae*, *Prodenia litura*, *Spodoptera spp.*, *Pieris spp.*, *Chilo spp.*, *Pyrausta nubilalis*, *Ephestia kuehniella*, *Galleria mellonella*, *Cacoecia podana*, *Homona magnanima* and *Tortrix viridana*;

from the order of the Coleoptera, for example *Rhizopertha dominica*, *Acanthoscelides obtectus*, *Diabrotica spp.*, *Epilachna varivestis*, *Oryzaephilus surinamensis*, *Anthonomus spp.*, *Sitophilus spp.*, *Cosmoplites sordidus*, *Dermestes spp.*, *Lyctus sop.*, *Ptinus spp.*, *Gibbium psylloides*, *Tribolium spp.*, *Tenebrio molitor* and *Agriotes spp.*;

from the order of the Hymenoptera, for example *Diprion spp.*, *Monomorium pharaonis* and *Vespa spp.*;

from the order of the Diptera, for example *Aedes spp.*, *Anopheles spp.*, *Culex spp.*, *Drosophila melanogaster*, *Musca spo.*, *Fannia spp.*, *Lucilia spp.*; *Chrysomya spp.*, *Stomoxys spp.*, *Oestrus spp.*, *Hypoderma spp.*, *Tabanus spp.*, *Bibio hortulanus*, *Phormia spp.* and *Pegomyia hyoscyami*;

from the order of the Siphonaptera, for example *Xenopsylla cheopis* and *Ceratophyllus spp.*

As is known from the above, the compound of the present invention has an extremely broad pesticidal spectrum and has especially strong pesticidal activity against those insect pests from the Diptera such as *Musca spp.*, those insect pests from the Homoptera such as *Laodelphax striatellus*, *Nephotettix cincticeps* and *Myzus persicae*, those insect pests from the Lepidoptera such as *Prodenia litura* and *Plutella maculipennis*, and those insect pests from the Coleoptera such as *Diabrotica spp.* The compound of the present invention is suitable for effectively combatting such pests as described above which are present, e.g. on vegetables, grains, fruit trees or in soil.

The compounds of the present invention as such may be used for the pesticidal purpose intended in the present invention. Further, the compounds of this invention may be formulated into preparations commonly employed as an insecticide, for example, powdery dusts, coarse dusts, fine granules, granules, wettable powders, emulsifiable concentrates, aqueous liquids, water soluble powders, oil suspensions and so on, with admixture of a carrier and, if desired, other auxiliary agents. The carrier or liquid media as used herein means a synthetic or natural and inorganic or organic substance that is mixed with an active compound and can assist an active compound in its arrival to the portion to be treated and make it easy to store, transport or handle.

As suitable solid carriers may be mentioned inorganic substances such as clays, which may be represented by Kaolinite, Montmorillonite, Bentonite or Attapulgite, talc, mica, pyrophyllite, pumice, vermiculite, gypsum, alumina, calcium carbonate, dolomite, diatomaceous earth, magnesium carbonate, apatite, zeolite, silicic anhydride, synthetic calcium silicate and the like, vegetable organic substances such as soybean meal, tobacco powder, walnut powder, wheat flour, wood meal, starch, crystalline cellulose and the like, synthetic or natural high polymer compounds such as cumarone resin, petroleum resin, alkyd resin, polyvinyl chloride, polyalkylene glycol, ketone resin, ester gum, copal gum, dammar gum and the like, waxes such as carnauba wax, beeswax and the like or urea.

As suitable liquid media or carriers may be mentioned paraffin or naphthene hydrocarbons such as kerosene, mineral oil, spindle oil, white oil and the like, aromatic hydrocarbons such as benzene, toluene, xylene, ethylbenzene, cumene, methylnaphthalene and the like, chlorinated hydrocarbons such as carbon tetrachloride, chloroform, trichloroethylene, monochlorobenzene, o-chlorotoluene and the like, ethers such as dioxane, tetrahydrofuran and the like, ketones such as acetone, methyl ethyl ketone, diisobutylketone, cyclohexanone, acetophenone, isophorone and the like, esters such as ethyl acetate, butyl acetate, amyl acetate, ethylene glycol acetate diethylene glycol acetate, dibutyl maleate, diethyl succinate and the like, alcohols such as methanol, ethanol, butanol, n-hexanol, ethylene glycol, diethylene glycol, cyclohexanol, benzyl alcohol and the like, ether alcohols such as ethylene glycol ethyl ether, ethylene glycol phenyl ether, diethylene glycol ethyl ether, diethylene glycol butyl ether and the like, nitriles such as acetonitrile and the like, polar solvents such as dimethylformamide, dimethylsulfoxide and the like or water.

With respect to surface active agents to be used for emulsifying, dispersing, wetting, spreading, binding, controlling disintegration, stabilizing active ingredient, improving fluidity, rust proofing and so on, those which are non-ionic, anionic, cationic and amphoteric may be used.

As examples of surface active agents to be used in the present invention, there may be mentioned polyoxyethylene alkyl ether, polyoxyethylene alkylaryl ether, polyoxyethylane fatty acid ester, sorbitan fatty acid ester, polyoxyethylene sorbitane fatty acid ester, polyoxyethylene, polyoxypropylene, polyoxyethylene alkylphosphate, fatty acid salt, alkylsulfuric acid ester, alkyl sulfonate, alkylaryl sulfonate, alkylphosporic acid ester, polyoxyethylene alkylsulfuric acid ester, quaternary ammonium salt, and oxyalkylamine. However, the surfactant is not restricted to these specific examples. In addition, gelatin, casein, sodium alginate, starch, agar or polyvinyl alcohol may optionally be employed as an auxiliary agent.

In general, the preparations exemplified above contain the compound of the present invention in an amount of from 5 to 50% by weight.

Wettable powders or emulsifiable concentrates may be applied at a rate of from 0.1 to 50 kg per hectare in a diluted form with from 200 to 2500 liters of water.

Granules or dusts as such may be applied at a rate of from 0.1 to 60 kg per hectare.

Moreover, the compound of the present invention may be combined with other pesticidal active ingredients to improve pesticidal activities. As examples of such other pesticidal active ingredients there may be mentioned, for example: MPP, i.e., 0,0-dimethyl O-4-methylthio-m-toryl thiophosphate; Diazinon, O,O-diethyl O-2-isopropyl-6-methylpyrimidin-4-yl phosphorothioate; ESP, S-2-ethylsulfinyl-1-methylethyl O,O-dimethyl dithiophosphate; Malathion, S-1,2-bis(ethoxycorbonyl)ethyl O,O-dimethyl dithiophosphate; Dimethoate, O,O-dimethyl S-methylcarbamoylmethyl phosphorodithioate; DDVP, 2,2-dichlorovinyl dimethyl phosphate; Acephate O,S-dimethyl N-acetyl-phosphoramidothiolate; Salithion, 2-methoxy-4H-1,3,2-benzodioxaphosphorin-2-sulfide; BPMC, O-sec-butyl-phenyl methylcarbamate; nicotine sulfate; Cartop, S,S'-[2(dimethylamino)trimethylene]bis(thiocarbamate); Allethrin, (1RS)-3-allyl-2-methyl-4-oxocyclopent-2-enyl(1RS,3RS; 1 RS,3RS)-2,2-dimethyl-3-(2-methyl-prop-1-enyl)cyclopropanecarboxylate; Methomyl, S-methyl N-(methylcarbamoyloxy)thioacetoimidate.

The above-mentioned pesticidally active ingredients are given only for exemplification. Therefore, pesticidally active ingredients which can be used in combination with the compound of the present invention, of course, are by no means restricted to them. Furter, the pesticide of the present invention can be used together with a fungicide, a herbicide, a plant growth regulator, a microbial pesticide or a fertilizer.

Now, with respect to the use of the compound of the present invention for combatting pests present on plants, an explanation will be given below.

Method for combatting Small brown planthopper

In May or June after the rice-planting, i.e. at the time when adults of small brown plant-hopper of the second generation appear in a paddy field, an emulsifiable concentrate or wettable powder comprising the compound of the present invention is diluted with a predetermined quantity of water and sprayed over the whole paddy field to control Small brown planthopper so that the rice plant is prevented from infection with stripe carried by this pest. In this case, it is preferable to use the compound of the present invention at a rate of from about 0.1 to 0.2 kg per hectare.

Method for combatting Green rice leafhopper

In May or June after the rice-planting, or in August or September, an emulsifiable concentrate or wettable powder comprising the compound of the present invention is diluted with water and sprayed over the whole paddy field in order to protect the rice plant from infection with stripe or damage due to suction of juice from the plant by Green rice leafhopper. In this case, the compound of the present invention is preferably used at a rate of from about 0.1 to 0.2 kg per hectare.

Method for combatting Tobacco cutworm

From summer to autumn, at the time when vegetables or crops in fields such as cabbage, eggplant, taro and soybean are growing, an emulsifiable concentrate or wettable powder comprising the compound of the present invention is diluted with water and sprayed over the whole field to combat Tobacco cut worm. In this case, the compound of the present invention is preferably used at a rate of from 0.2 to 0.3 kg.

Method for combatting Green peach aphid

From spring to autumn, at the time when fruit trees such as peach trees are foliate or vegetables such as cabbage, Japanese radish and Chinese cabbage are growing, an emulsifiable concentrate or wettable powder comprising the compound of the present invention is diluted with a predetermined quantity of water and sprayed over the fruit trees and the whole field to control Green peach aphid. For the orchard, the compound of the present invention is preferably used at a rate of from 0.2 to 0.6 kg per hectare. For the field, the compound of the present invention is preferably used at a rate of from 0.1 to 0.2 kg per hectare.

It is noted that the compound of the present invention can be employed for combatting not only pests present on plants, or on other places overground, but also those or larvae thereof present underground, which may also affect the growth of plants. That is, the compound of the present invention can also be employed for combatting a variety of pests dwelling in soil such as species of Diabrotica, e.g. *Diabrotica virgifera virgifera*, *D. longicornia barberi* and *D. undecimpunctata howardi*, which are called western, northern and southern corn rootworms, respectively.

For use as soil pesticides, the compound of the present invention may be suitably applied to the soil at a rate of from about 0.1 to about 10 kg per hectare. Further, the compound of the present invention may be formulated for use as a granule or a dust and, for more effective control of pests, it may be physically lightly mixed with the topsoil. The mixing is followed or immediately preceded by planting seeds. Alternatively, the compound of the present invention may be applied to soil as a drench which can be prepared by diluting an emulsifiable concentrate of the present compound with water. In application of the compound of the present invention, it may be sprayed on the surface of farm land in a striped pattern or incorporated into soil by either applying the compound on farm land simultaneously with furrowing or applying the compound on farm land before cultivation as in the application of a fertilizer.

The present invention will now be described in more detail by the following the Examples and Comparative Examples, which should not be construed to be limiting the scope of the present invention. The compound Nos. indicated in Table 1 are commonly referred to in the Examples and Comparative Examples.

EXAMPLE 1

(A) Synthesis of N-ethyl-N-isopropoxycarbonylmethylphosphonamidethioyl chloride.

15 g of methylphosphonothioic dichloride, 13.2 g of isopropyl N-ethylcarbamate and 10.1 g of triethylamine were added to 80 ml of dried dioxane and the mixture was reacted under reflux at 101° C. for 2 hours to form precipitates. Then, the precipitates were removed by filtration and the solvent was then removed by distillation under vacuum, followed by purification of the residue by column chromatography (developer: hexane/ethyl acetate). As a result, 13.6 g of N-ethyl-N-isopropoxy-carbonylmethylphosphonamidethioyl chloride was obtained as an intermediate (yield : 65.7%)

(B) Synthesis of N-ethyl-N-isopropoxycarbonyl-O-4-cyanophenylmethylphosphonamidothionate (Compound No. 11)

1.5 g of the above-obtained N-ethyl-N-isopropoxycarbonylmethylphosphonamidethioyl chloride, 0.8 g of 4-cyanophenol and 1.2 g of triethylamine were added to 25 ml of dried tetrahydrofuran and the mixture was reacted at 10° C. for 15 hours while stirring to form precipitates. The precipitates were removed by filtration and the solvent was then removed by distillation under vacuum, followed by purification of the residue by column chromatography (developer: hexane/ethyl acetate). As a result, 1.2 g of N-ethyl-N-isopropoxy carbonyl-O4-cyanophenylmethylphosphonamidothionate, which is the desired product, was obtained (yield : 60%)

The same procedure as described above was repeated except that the raw materials were varied, thereby obtaining various compounds as shown in Table 1. Characterization of the thus obtained compounds was conducted by NMR spectrum (using PMX-60Si and FX-100 manufactured by JEOL LTD., Japan) and IR spectrum (using IR-408 manufactured by Shimadzu Corp., Japan).

TABLE 1

$$CH_3-P\overset{S}{\underset{OR^3}{\|}}\underset{}{\overset{N}{\diagdown}}\overset{R^1}{\underset{COOR^2}{\diagup}}$$

| Compound No. | $R^1$ | $R^2$ | $R^3$ | Physical properties | $^1H$—NMR Spectral data CDCl$_3$ (ppm) |
|---|---|---|---|---|---|
| 1 | $CH_3$ | $i-C_3H_7$ | 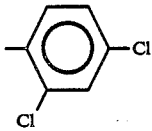 | Viscous liquid | 1.33(d, 6H), 2.49(d, 3H), 3.27(d, 3H), 5.13(m, 1H), 6.95~7.60(m, 3H) |
| 2 | $CH_3$ | $i-C_3H_7$ | $CH_3$ | Viscous liquid | 1.35(d, 6H), 2.20(d, 3H), 3.27(d, 3H), 3.66(d, 3H), 5.10(m, 1H), |
| 3 | $CH_3$ | $i-C_3H_7$ | 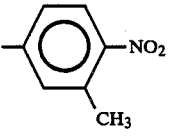 | Viscous liquid | 1.34(d, 6H), 2.43(d, 3H), 2.49(s, 3H), 5.15(m, 1H), 7.00~8.30(m, 3H) |
| 4 | $CH_3$ | $i-C_3H_7$ | 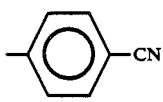 | Viscous liquid | 1.30(d, 6H), 2.40(d, 3H), 3.27(d, 3H), 5.09(m, 1H), 7.10~7.85(m, 4H) |

TABLE 1-continued $$\underset{OR^3}{\underset{|}{CH_3-P}}\overset{S}{\underset{\|}{\vphantom{|}}}\underset{COOR^2}{\overset{R^1}{\diagup}}N$$

| Compound No. | $R^1$ | $R^2$ | $R^3$ | Physical properties | $^1H$—NMR Spectral data CDCl$_3$ (ppm) |
|---|---|---|---|---|---|
| 5 | CH$_3$ | i-C$_3$H$_7$ | 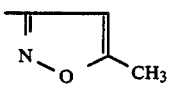 | Viscous liquid | 1.33(d, 6H), 2.43(s, 3H), 2.50(d, 3H), 3.35(d, 3H), 5.15(m, 1H), 6.02(s, 1H) |
| 6 | CH$_3$ | i-C$_3$H$_7$ | C$_2$H$_5$ | Viscous liquid | 1.32(t, 3H), 1.37(d, 6H), 2.35(d, 3H), 3.43(d, 3H), 4.13(m, 2H), 5.09(m, 1H) |
| 7 | CH$_3$ | i-C$_3$H$_7$ | 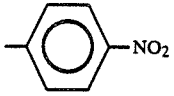 | Viscous liquid | 1.33(m, 6H), 2.42(d, 3H), 3.22(d, 3H), 5.03(m, 1H), 7.08~8.35(m, 4H) |
| 8 | CH$_3$ | i-C$_3$H$_7$ | 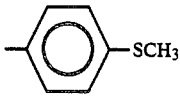 | Viscous liquid | 1.30(d, 6H), 2.30(d, 3H), 2.41(s, 3H), 3.15(d, 3H), 5.02(m, 1H), 6.80~7.33(m, 4H) |
| 9 | C$_2$H$_5$ | i-C$_3$H$_7$ | 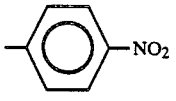 | mp (°C.) 35 or lower | 1.00(t, 3H), 1.32(d, 6H), 2.33(d, 3H), 3.80(m, 1H), 5.08(m, 1H), 7.10~8.45(m, 4H) |
| 10 | C$_2$H$_5$ | i-C$_3$H$_7$ | 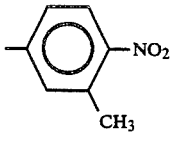 | Viscous liquid | 1.00(t, 3H), 1.31(d, 6H), 2.33(d, 3H), 2.60(s, 3H), 3.80(m, 2H), 5.08(m, 1H), 6.95~8.18(m, 3H) |
| 11 | C$_2$H$_5$ | i-C$_3$H$_7$ | 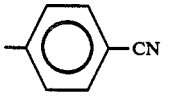 | Viscous liquid | 0.97(t, 3H), 1.32(d, 6H), 2.33(d, 3H), 3.80(m, 2H), 5.06(m, 1H), 7.10~7.85(m, 4H) |
| 12 | C$_2$H$_5$ | i-C$_3$H$_7$ | CH$_3$ | Viscous liquid | 1.20(t, 3H), 1.32(d, 6H), 2.17(d, 3H), 3.63(d, 3H), 3.90(m, 1H), 5.10(m, 1H) |
| 13 | C$_2$H$_5$ | i-C$_3$H$_7$ | C$_2$H$_5$ | Viscous liquid | 0.95~1.57(m, 12H), 2.17(d, 3H), 3.55~4.50(m, 4H), 5.07(m, 1H) |
| 14 | C$_2$H$_5$ | i-C$_3$H$_7$ | 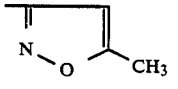 | Viscous liquid | 0.85~1.50(m, 9H), 2.35(d, 3H), 2.40(s, 3H), 3.80(m, 2H), 5.05(m, 1H), 5.97(s, 1H) |
| 15 | C$_2$H$_5$ | i-C$_4$H$_9$ | 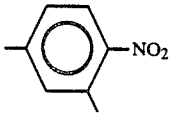 | Viscous liquid | 0.75~1.25(m, 9H), 2.01(m, 1H), 2.33(d, 6H), 2.60 (s, 3H), 3.85(m, 2H), 4.03(d, 2H), 6.95~8.18(m, 3H) |
| 16 | C$_2$H$_5$ | i-C$_4$H$_9$ | 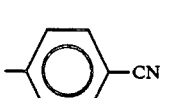 | Viscous liquid | 0.70~1.30(m, 9H), 1.95(m, 1H), 2.37(d, 3H), 3.80(m, 2H), 4.10(d, 2H), 7.20~8.00(m, 4H) |
| 17 | C$_2$H$_5$ | i-C$_4$H$_9$ | 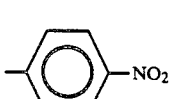 | mp (°C.) 40.5 | 0.75~1.20(m, 9H), 2.00(m, 1H), 2.34(d, 3H), 3.80(m, 2H), 4.03(d, 2H), 7.15~8.35(m, 4H) |

TABLE 1-continued $$CH_3-P(=S)(OR^3)-N(R^1)-COOR^2$$

| Compound No. | $R^1$ | $R^2$ | $R^3$ | Physical properties | $^1H$—NMR Spectral data CDCl$_3$ (ppm) |
|---|---|---|---|---|---|
| 18 | $C_2H_5$ | i-$C_4H_9$ | 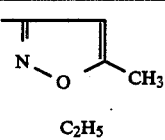 | Viscous liquid | 0.70~1.30(m, 9H), 2.00(m, 1H), 2.30(d, 3H), 2.37(s, 3H), 3.85(m, 2H), 4.00(d, 2H), 5.93(s, 1H) |
| 19 | $C_2H_5$ | i-$C_4H_9$ | $C_2H_5$ | Viscous liquid | 0.76~1.50(m, 12H), 1.95(m, 1H), 2.17(d, 3H), 3.53~4.43(m, 6H) |
| 20 | $C_2H_5$ | i-$C_4H_9$ | $CH_3$ | Viscous liquid | 0.78~1.40(m, 9H), 1.90(m, 1H), 2.10(d, 3H), 3.30~4.15(m, 7H) |
| 21 | $C_2H_5$ | n-$C_3H_7$ | 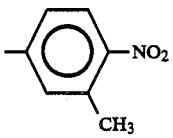 | Viscous liquid | 0.78~1.30(m, 6H), 1.75(m, 2H), 2.43(d, 3H), 2.65(s, 3H), 3.60~4.50(m, 4H), 7.10~8.37(m, 3H) |
| 22 | $C_2H_5$ | n-$C_3H_7$ | 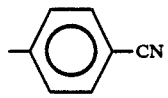 | Viscous liquid | 0.78~1.33(m, 6H), 1.80(m, 2H), 2.45(d, 3H), 3.60~4.55(m, 4H), 7.30~8.10(m, 4H) |
| 23 | $C_2H_5$ | n-$C_3H_7$ | 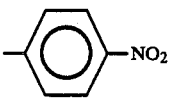 | Viscous liquid | 0.75~1.25(m, 6H), 1.70(m, 2H), 2.40(d, 3H), 3.55~4.45(m, 4H), 7.20~8.50(m, 4H) |
| 24 | $C_2H_5$ | N—$C_3H_7$ | 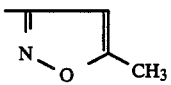 | Viscous liquid | 0.70~2.65(m, 14H), 3.60~4.40(m, 4H), 6.05(s, 1H) |
| 25 | $C_2H_5$ | $C_2H_5$ | 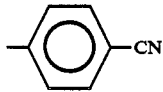 | Viscous liquid | 1.02(t, 3H), 1.34(t, 3H), 2.35(d, 3H), 3.82(m, 2H), 4.33(q, 2H), 7.16~7.90(m, 4H) |
| 26 | $C_2H_5$ | $C_2H_5$ | 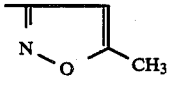 | Viscous liquid | 0.85~1.45(m, 6H), 2.33(d, 6H), 2.37(s, 3H), 3.80(m, 2H), 4.27(q, 2H), 5.94(s, 1H) |
| 27 | $C_2H_5$ | $C_2H_5$ | $C_2H_5$ | Viscous liquid | 0.95~1.56(m, 9H), 2.20(d, 3H), 3.55~4.66(m, 6H) |
| 28 | $C_2H_5$ | $C_2H_5$ | 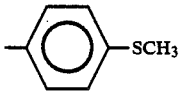 | Viscous liquid | 0.99(t, 3H), 1.33(t, 3H), 2.30(d, 3H), 2.40(s, 3H), 3.75(m, 2H), 4.25(q, 2H), 6.88~7.30(m, 3H) |
| 29 | $C_2H_5$ | i-$C_3H_7$ | 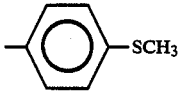 | Viscous liquid | 0.98(t, 3H), 1.35(d, 6H), 2.33(d, 3H), 2.44(s, 3H), 3.52~3.98(m, 2H), 5.04(m, 1H), 6.85~7.34(m, 4H) |
| 30 | $C_2H_5$ | $CH_3$ | $C_2H_5$ | Viscous liquid | 1.13(t, 3H), 1.28(t, 3H), 2.15(d, 3H), 3.45~4.36(m, 7H) |
| 31 | $C_2H_5$ | $CH_3$ | 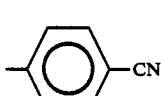 | Viscous liquid | 1.04(t, 3H), 1.36(d, 3H), 3.45~4.25(m, 5H), 6.95~7.80(m, 4H) |

TABLE 1-continued $$\text{CH}_3-\underset{\underset{OR^3}{|}}{\overset{\overset{S}{\|}}{P}}-\underset{\underset{COOR^2}{}}{\overset{R^1}{N}}$$

| Compound No. | R¹ | R² | R³ | Physical properties | ¹H—NMR Spectral data CDCl₃ (ppm) |
|---|---|---|---|---|---|
| 32 | C₂H₅ | CH₃ | (5-methylisoxazol-3-yl) | Viscous liquid | 1.16(t, 3H), 1.36(s, 3H), 1.38(d, 3H), 3.50~4.30(m, 5H), 5.95(s, 1H) |
| 33 | C₂H₅ | CH₃ | (4-nitro-2-methylphenyl) | Viscous liquid | 1.05(t, 3H), 2.40(d, 3H), 2.60(s, 3H), 3.50~4.26(m, 5H), 6.90~8.18(m, 3H) |
| 34 | n-C₃H₇ | i-C₃H₇ | (4-nitro-2-methylphenyl) | Viscous liquid | 0.85(t, 3H), 1.05~1.85(m, 8H), 2.35(d, 3H), 2.60(s, 3H), 3.70(m, 2H), 5.10(m, 1H), 7.00~8.20 (m, 3H) |
| 35 | n-C₃H₇ | i-C₃H₇ | CH₃ | Viscous liquid | 0.90(t, 3H), 1.10~1.95(m, 8H), 2.20(d, 3H), 3.40~4.15(m, 5H), 5.16(m, 1H) |
| 36 | n-C₃H₇ | i-C₃H₇ | (4-cyanophenyl) | Viscous liquid | 0.90(t, 3H), 1.10~1.85(m, 8H), 3.70(m, 2H), 5.10(m, 1H), 7.13~7.90(m, 4H) |
| 37 | n-C₃H₇ | i-C₃H₇ | C₂H₅ | Viscous liquid | 0.85(t, 3H), 1.05~1.90(m, 11H), 2.15(d, 3H), 3.90(m, 4H), 5.08(m, 1H) |
| 38 | n-C₃H₇ | i-C₃H₇ | (5-methylisoxazol-3-yl) | Viscous liquid | 0.87(t, 3H), 1.07~1.90(m, 8H), 2.10~2.60(m, 6H), 3.85(m, 2H), 5.10(m, 1H), 5.99(s, 1H) |
| 39 | n-C₃H₇ | i-C₃H₇ | (2,4-dichlorophenyl) | Viscous liquid | 0.85(t, 3H), 1.10~1.90(m, 8H), 2.40(d, 3H), 3.75 (m, 2H), 5.08(m, 1H), 7.13~7.58(m, 3H) |
| 40 | n-C₃H₇ | sec-C₄H₉ | (4-nitrophenyl) | Viscous liquid | |
| 41 | n-C₃H₇ | sec-C₄H₉ | (4-cyanophenyl) | Viscous liquid | |
| 42 | n-C₃H₇ | sec-C₄H₉ | (4-nitro-2-methylphenyl) | Viscous liquid | |
| 43 | i-C₃H₇ | C₂H₅ | (4-nitrophenyl) | mp (°C.) 64.0 | 0.95~1.60(m, 9H), 2.35(d, 3H), 4.30(q, 2H), 4.85(m, 1H), 7.14~8.45(m, 4H) |

TABLE 1-continued

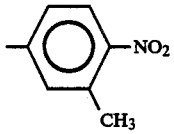

| Compound No. | R¹ | R² | R³ | Physical properties | ¹H—NMR Spectral data CDCl₃ (ppm) |
|---|---|---|---|---|---|
| 44 | i-C₃H₇ | C₂H₅ | 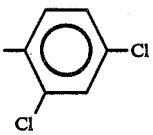 | Viscous liquid | 1.00~1.60(m, 9H), 2.30(d, 3H), 2.58(s, 3H), 4.28(q, 4H), 4.90(m, 1H), 6.80~8.15(m, 3H) |
| 45 | i-C₃H₇ | C₂H₅ | 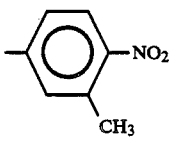 | Viscous liquid | 1.15~1.70(m, 9H), 2.43(d, 3H), 4.30(q, 2H), 4.95(m, 1H), 7.10~7.55(m, 3H) |
| 46 | i-C₃H₇ | i-C₃H₇ | 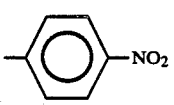 | Viscous liquid | 0.92~1.50(m, 12H), 2.35(d, 3H), 2.57(s, 3H), 4.42~5.33(m, 2H), 6.85~8.10(m, 3H) |
| 47 | i-C₃H₇ | i-C₃H₇ | (p-NO₂-phenyl) | Viscous liquid | 0.95~1.55(m, 12H), 2.43(d, 3H), 5.07(m, 2H), 7.15~8.50(m, 4H) |

EXAMPLE 2

(Preparation of an emulsifiable concentrate)

10 parts of the present compound, 5 parts of surfactant No. 1074 (produced and sold by TAKEMOTO OIL AND FATS CO., LTD, Japan) and 5 parts of surfactant No. 1075 (produced and sold by TAKEMOTO OIL AND FATS CO., LTD, Japan) were dissolved in a solvent mixture of xylene and cyclohexane (9:1, v/v), to thereby prepare a 10% (w/v) emulsifiable concentrate.

EXAMPLE 3

(Preparation of a wettable powder)

10 parts of the present compound, 75 parts of talc, 10 parts of white carbon and 5 parts of Sorpol 5039 (trade name of a surfactant produced and sold by TOHO CHEMICAL INDUSTRY CO., LTD., Japan) were well ground and mixed in an agate mortar, to thereby prepare a 10% (w/w) wettable powder.

EXAMPLE 4 AND COMPARATIVE EXAMPLE (Pesticidal test on Laodelphax striatellus)

The present wettable powders of various compounds indicated in Table 2 were dissolved in water to prepare aqueous solutions having compound concentrations indicated in Table 2. Then, rice plants in the 4 to 8 leaf stage and of about 15 cm in length were dipped in each of the aqueous solutions and then taken out, followed by air-drying. Then, the rice plants were each separately put in test tubes each containing about 2 ml of water, test pests were introduced thereinto by 10 insects per test tube and the top of each test tube was covered with a polyester cloth. The test tubes were kept at 25° C. and allowed to stand for 48 hours. After that period, the number of dead pests was counted. The above procedure was conducted three times in total and an average of the data was obtained. The results are shown in Table 2.

For comparison, another pesticidal test was conducted in substantially the same manner as described above except that S-1,2-bis(ethoxycarbonyl) ethyldimethylphosphorothiorothionate (Malathion, common name of a pesticide produced and sold by Augusta Chemical Co., U.S.A.) was employed in place of the present compound. The results are shown in Table 2.

TABLE 2

|  | Concentration (ppm) | Death rate (%) |
|---|---|---|
| Compound No. 24 | 500 | 100 |
|  | 50 | 100 |
| Compound No. 27 | 500 | 100 |
|  | 50 | 100 |
| Compound No. 46 | 500 | 100 |
|  | 50 | 100 |
| Compound No. 47 | 500 | 100 |
|  | 50 | 100 |
| Comparative Example 1 | 50 | 98 |

EXAMPLE 5 AND COMPARATIVE EXAMPLE 2

(Pesticidal test on *Prodenia litura*)

The present wettable powders of various compounds indicated in Table 3 were dissolved in water to prepare aqueous solutions having compound concentrations indicated in Table 3. Filter papers were set on both the upper halves and the lower halves of petri dishes and 2 ml of each of the aqueous solutions was separately added dropwise onto both of the filter papers in the petri dishes by means of a pipette. In this instance, a piece of agar containing an artificial food for *Prodenia litura* had been applied onto each of the upper filter papers set on the upper halves of the petri dishes before the above-mentioned solutions were added. After the addition of the aqueous solutions of the present compounds, the filter papers were allowed to stand for about one hour in order to dry them. Then the test pests (one-year old larvae) were introduced onto the filter papers set on the lower halves of the dishes by 10 insects per dish and the upper halves of the dishes were placed thereon. The petri dishes were kept at 25° C. and allowed to stand for 48 hours. After that period, the number of dead pests was counted. The above procedure was conducted three times in total and an average of the data was obtained. The results are shown in Table 3.

For comparison, another pesticidal test was conducted in substantially the same manner as described above except that S-1,2-bis(ethoxycarbonyl) ethyldimethylphosphorothiothionate (Malathion, common name of a pesticide produced and sold by Augusta Chemical Co., U.S.A.) was employed in place of the present compound. The results are shown in Table 3.

TABLE 3

|  | Concentration (ppm) | Death rate |
|---|---|---|
| Compound No. 9 | 1000 | 100 |
|  | 100 | 73 |
| Compound No. 15 | 1000 | 100 |
|  | 100 | 73 |
| Compound No. 16 | 1000 | 100 |
|  | 100 | 97 |
| Compound No. 17 | 1000 | 100 |
|  | 100 | 100 |
| Compound No. 21 | 1000 | 100 |
|  | 100 | 100 |
| Compound No. 22 | 1000 | 100 |
|  | 100 | 100 |
| Compound No. 47 | 1000 | 100 |
|  | 100 | 100 |
| Comparative Example 2 | 100 | 40 |

EXAMPLE 6 AND COMPARATIVE EXAMPLE 3

(Comparative test with a comparative compound)

With respect to the present compounds and comparative compounds, the pesticidal activities against *Laodelphax striatellus* and *Prodenia litura* were examined and compared in substantially the same manner as in comparison of Example 4 with Comparative Example 1 and comparison of Example 5 with Comparative Example 2, respectively, except that the employed compounds and concentrations thereof were as indicated in Table 4. The results are shown in Table 4.

TABLE 4

|  | Concentration (ppm) | Death rate(%) Laodelphax striatellus | Death rate(%) Prodenia litura |
|---|---|---|---|
| Compound No. 47 | 400 | 100 | 100 |
|  | 200 | 100 | 100 |
|  | 100 | 100 | 100 |
|  | 50 | 100 | 87 |
| Comparative Example 3 | 400 | 70 | 13 |
|  | 200 | 10 | 0 |
|  | 100 | 0 | 0 |
|  | 50 | 0 | 0 |

The formula of the comparative compound $$\begin{array}{c} CH_3P \underset{O}{\overset{S}{\parallel}} \diagdown \!\!\! \diagup \overset{H}{\underset{\diagdown}{N}} \!\!\! \diagdown COOi\text{-}C_3H_7 \\ \diagdown O\text{-}\langle \text{phenyl} \rangle \text{-}NO_2 \end{array}$$

EXAMPLE 7 AND COMPARATIVE EXAMPLE 4

(Test of the maintenance of the pesticidal activity, using *Laodelphax striatellus*)

In the same manner as in Example 4 and Comparative Example 1, rice plants were separately treated with each of 250 ppm solutions prepared by dissolving in water the present compounds and comparative compound which are indicated in Table 5 and then put in test tubes, and test pests were introduced into test tubes. The tops of the test tubes were covered with cloths and the test tubes were then kept at 25° C. for 48 hours, after which the number of dead pests was counted. In the above experiments, however, the treated rice plants were allowed to stand in the test tubes at room temperature for several lengths of period as indicated in Table 5 before the introduction of test pests into the test tubes. The pesticidal activity-maintaining effects were evaluated based on the death rates in relation to the time lengths between the treatment with compounds and the introduction of the test pests. The results are shown in Table 5.

TABLE 5

|  | Concentration (ppm) | Death rates in relation to the time lengths between the treatment with compounds and the introduction of the test pests | | | |
|---|---|---|---|---|---|
|  |  | immediate | 3 days | 7 days | 14 days |
| Compound No. 47 | 250 | 100 | 100 | 100 | 43 |
| Compound No. 46 | 250 | 100 | 97 | 13 | 0 |
| Comparative Example 4 | 250 | 100 | 20 | 0 | 0 |

What is claimed is:

1. A phosphonamidothionate derivative represented by the formula

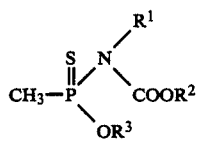  (I)

wherein $R^1$ and $R^2$ each independently represent a straight-chain alkyl group having 1 to 4 carbon atoms or a branched alkyl group having 3 or 4 carbon atoms and $R^3$ represents a phenyl group unsubstituted or substituted with a chlorine atom, a methyl group, a nitro group, a methylthio group or a nitrile group, an alkyl group having 1 to 4 carbon atoms or a 5-methyl-2-isoxazolyl group.

2. The phosphonamidothionate derivative according to claim 1, wherein $R^1$ represents a straight-chain alkyl group having 2 or 3 carbon atoms or an isopropyl group, $R^2$ represents a straight-chain alkyl group having 2 or 3 carbon atoms or a branched alkyl group having 3 or 4 carbon atoms and $R^3$ represents a 4-nitrophenyl group, a 3-methyl-4-nitrophenyl group, a 4-cyanophenyl group, an ethyl group or a 5-methyl-2-isoxazolyl group.

3. The phosphonamidothionate derivative according to claim 2, wherein $R^1$ and $R^2$ each represent an isopropyl group and $R^3$ represents a 4-nitrophenyl group.

4. A process for preparing a phosphonamidothionate derivative represented by the formula

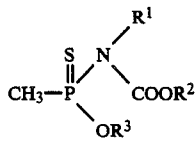  (I)

wherein $R^1$ and $R^2$ each independently represent a straight-chain alkyl group having 1 to 4 carbon atoms or a branched alkyl group having 3 or 4 carbon atoms and $R^3$ represents a phenyl group unsubstituted or substituted with a chlorine atom, a methyl group, a nitro group, a methylthio group or a nitrile group, an alkyl group having 1 to 4 carbon atoms or a 5-methyl-2-isoxazolyl group, which comprises the steps of (1) reacting a carbamic acid ester derivative represented by the formula

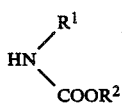  (II)

wherein $R^1$ and $R^2$ each independently represent a straight-chain alkyl group having 1 to 4 carbon atoms or a branched alkyl group having 3 or 4 carbon atoms, with methylphosphonothioic dichloride in dioxane in the presence of an amine, to thereby obtain a methylphosphonothioyl chloride derivative represented by the formula

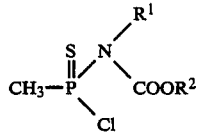  (III)

wherein $R^1$ and $R^2$ are as defined above, and (2) subsequently reacting the methylphosphonothioyl chloride derivative of formula (III) with a compound represented by the formula $$HO-R^3 \quad (IV)$$

wherein $R^3$ represents a phenyl group unsubstituted or substituted with a chlorine atom, a methyl group, a nitro group, a methylthio group or a nitrile group, an alkyl group having 1 to 4 carbon atoms or a 5-methyl2-isoxazolyl group, in tetrahydrofuran in the presence of an amine.

5. A pesticidal composition comprising as an active ingredient a pesticidally effective amount of a phosphonamidothionate derivative represented by the formula

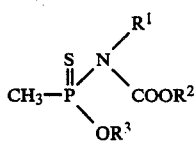  (I)

wherein $R^1$ and $R^2$ each independently represent a straight-chain alkyl group having 1 to 4 carbon atoms or a branched alkyl group having 3 or 4 carbon atoms and $R^3$ represents a phenyl group unsubstituted or substituted with a chlorine atom, a methyl group, a nitro group, a group having 1 to 4 carbon atoms or a 5-methyl-2-isoxazolyl group, and a sanitary or agriculturally and horticulturally acceptable carrier or diluent.

6. The pesticidal composition according to claim 5, wherein $R^1$ represents a straight-chain alkyl group having 2 or 3 carbon atoms or an isopropyl group, $R^2$ represents a straight-chain alkyl group having 2 or 3 carbon atoms or a branched alkyl group having 3 or 4 carbon atoms and $R^3$ represents a 4-nitrophenyl group, a 3-methyl-4-nitrophenyl group, a 4-cyanophenyl group, an ethyl group or a 5-methyl-2-isoxazolyl group.

7. The pesticidal composition according to claim 6, wherein $R^1$ and $R^2$ each represent an isopropyl group and R represents a 4-nitrophenyl group.

8. A method for combatting sanitary insect pests or agricultural and horticultural insect pests, which comprises applying to the insect pests or a habitat thereof a pesticidally effective amount of a phosphonamidothionate derivative represented by the formula

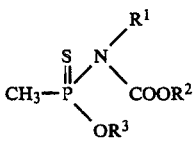  (I)

wherein $R^1$ and $R^2$ each independently represent a straight-chain alkyl group having 1 to 4 carbon atoms or a branched alkyl group having 3 or 4 carbon atoms and $R^3$ represents a phenyl group unsubstituted or substituted with a chlorine atom, a methyl group, a nitro group, a methylthio group or a nitrile group, an alkyl group having 1 to 4 carbon atoms or a 5-methyl-2-isoxazolyl group.

9. The method according to claim 8, wherein said sanitary insect pests are those belonging to *Diptera*.

10. The method according to claim 8, wherein said agricultural and horticultural insect pests are those belonging to *Homoptera* or *Lepidoptera*.

11. The method according to claim 8, wherein $R^1$ represents a straight-chain alkyl group having 2 or 3 carbon atoms or an isopropyl group, $R^2$ represents a straight-chain alkyl group having 2 or 3 carbon atoms or a alkyl group having 3 or 4 carbon atoms and $R^3$ represents a 4-nitrophenyl group, a 3-methyl-4-nitrophenyl group, a 4-cyanophenyl group, an ethyl group or a 5-methyl-2-isoxazolyl group.

12. The method according to claim 11, wherein $R^1$ and $R^2$ each represent an isopropyl group and $R^3$ represents a 4-nitrophenyl group.

* * * * *